(12) United States Patent
Mihashi

(10) Patent No.: US 7,566,131 B2
(45) Date of Patent: Jul. 28, 2009

(54) REFRACTION MEASURING INSTRUMENT

(75) Inventor: Toshifumi Mihashi, Tokyo (JP)

(73) Assignee: Kabushiki Kaisha Topcon, Itabashi-ku (JP)

( * ) Notice: Subject to any disclaimer, the term of this patent is extended or adjusted under 35 U.S.C. 154(b) by 333 days.

(21) Appl. No.: 10/549,854

(22) PCT Filed: Mar. 31, 2004

(86) PCT No.: PCT/JP2004/004702

§ 371 (c)(1),
(2), (4) Date: Sep. 23, 2005

(87) PCT Pub. No.: WO2004/086962

PCT Pub. Date: Oct. 14, 2004

(65) Prior Publication Data

US 2006/0215111 A1    Sep. 28, 2006

(30) Foreign Application Priority Data

Mar. 31, 2003   (JP) ............................. 2003-096215

(51) Int. Cl.
A61B 3/14 (2006.01)
A61B 3/10 (2006.01)

(52) U.S. Cl. ................... 351/209; 351/205; 351/211; 351/221

(58) Field of Classification Search ............ 351/209, 351/200, 205–207, 211, 220, 221
See application file for complete search history.

(56) References Cited

U.S. PATENT DOCUMENTS 4,355,871 A * 10/1982 Nevyas et al. ............... 351/212

(Continued)

FOREIGN PATENT DOCUMENTS

JP   62-8730   1/1987

(Continued)

OTHER PUBLICATIONS

Japanese Office Action issued Apr. 11, 2007 in JP-2003-096215.

*Primary Examiner*—William C Choi
*Assistant Examiner*—Jack Dinh
(74) *Attorney, Agent, or Firm*—Edwards Angell Palmer & Dodge LLP

(57) ABSTRACT

A refraction measuring instrument for measuring the refraction of an eye to be examined while the subject is viewing an external object in a more natural posture. A measuring light beam from a light source 21 is reflected from a mirror 25, shaped into a beam with a ring cross section, directed to a free curved surface prism 31 along an optical axis O2, reflected from a surface 31b and a beam splitting surface 31a, guided to an eye E along an optical axis O1 together with the visible light from outside the instrument, and form a ring pattern on the fundus F. The measurement beam reflected from the fundus F is received by a CCD 23 through the free curved surface prism 31 and a prism 22, and a ring pattern is imaged. A calculation control device 4 analyzes the imaged ring pattern and calculates the sphericity, the degree of astigmatism, and the astigmatic axis angle. For measurement, the subject A wears the refraction measuring instrument 1 on the head H through a wearing section 1a.

3 Claims, 5 Drawing Sheets

U.S. PATENT DOCUMENTS 6,761,454 B2 * 7/2004 Lai et al. .................... 351/216

FOREIGN PATENT DOCUMENTS

| JP | 3-21222 | 1/1991 |
| JP | 9-185009 | 7/1997 |
| JP | 11-332830 | 12/1999 |
| JP | 2001-161644 | 6/2001 |
| JP | 2002-512100 | 4/2002 |

* cited by examiner

REFRACTION MEASURING INSTRUMENT

TECHNICAL FIELD

The present invention relates to a refraction measuring instrument for measuring the refraction of an eye to be examined, and more particularly to a refraction measuring instrument capable of measuring the refraction of an eye to be examined while a subject is viewing the surrounding ambience, an image, or the like in a natural posture.

BACKGROUND ART

A refraction measuring instrument which is widely used at present normally includes a chin rest on which the chin of a subject is placed and a head rest to which the forehead of the subject abuts (see, for example, JP 11-299733 A) in order to prevent a relative position difference between the subject and the refraction measuring instrument. In such a refraction measuring instrument, the measurement is performed on the subject in an unnatural posture in which the subject slouches and the chin and the forehead are in contact with the chin rest and the head rest, respectively. Therefore, physical and mental burdens are placed on the subject. In addition, it is difficult to accurately measure the refraction of an eye to be examined in actual life.

In recent years, the development in the fields of image display devices, such as the development of three-dimensional displays is remarkable. A novel image display device achieves various effects by taking advantages of the structure of the human eye and the action thereof. In the example of the three-dimensional display, a stereoscopic image is to be displayed on a screen based on a parallax between the right eye and the left eye.

According to such a visual effect, sort of impractical operation may be forced to the eyes, so that the burden on the eyes becomes very large. Therefore, in order to display an eye-friendly image in view of human engineering, further research and development are proceeding at the present time. Thus, an instrument for measuring an accommodation state of the eyes viewing an image is required.

The refraction measuring instrument requires various conditions. Firstly, it is necessary to measure the refraction of each of the eyes to be examined while the eyes visually recognize the image displayed on the image display device. Secondly, the image display device is used in actual life, so it is necessary to perform the measurement in the natural posture based on the actual life. In the conventional refraction measuring instrument as disclosed in JP 11-299733 A, it may be difficult to satisfy this condition as described above. Thirdly, a person viewing the image does not necessarily stay in a predetermined position, so it is preferable to employ a structure capable of performing the measurement even when the person is moving from one place to another. However, a refraction measuring instrument having such a function has not been disclosed up to now. Fourthly, the image displayed on the image display device is a moving picture in many cases, so it is suitable to be able to continuously measure the eyes viewing the moving picture. An example of a refraction measuring instrument capable of performing real time measurement is disclosed in JP 2000-262475 A. In the refraction measuring instrument described in JP 2000-262475 A, it is difficult to satisfy the third condition in view of size thereof.

As a result, according to the refraction measuring instrument which is currently used, it is concluded that it is very difficult to achieve a purpose for making the assessment of the image display device.

Therefore, the present invention has been made in view of the above-mentioned problems. An object of the present invention is to provide a refraction measuring instrument capable of measuring the refraction of an eye to be examined while a subject is viewing an object outside the instrument, such as the surrounding ambience of the subject or an image.

Another object of the present invention is to provide a refraction measuring instrument capable of measuring the refraction of the eye to be examined in a more-natural posture.

Another object of the present invention is to provide a refraction measuring instrument capable of measuring the refraction even when the subject is moving.

In addition to the two objects, another object of the present invention is to provide a refraction measuring instrument capable of measuring the refraction in real time.

It is to be noted that the refraction measuring instrument according to the present invention can be suitably used for the assessment of an image display device such as a three-dimensional display in addition to normal measurement for prescribing spectacles or contact lenses.

DISCLOSURE OF THE INVENTION

In order to achieve the above-mentioned objects, according to the first feature of the invention, there is provided a refraction measuring instrument which includes: measuring means that has a light source for emitting a measurement light beam to an eye to be examined and performs objective measurement on refraction of the eye to be examined based on reflection light of the measurement light beam emitted from the light source, which is reflected on the eye to be examined; and an optical system for simultaneously guiding the measurement light beam emitted from the light source and visible light incident thereon from an outside to the eye to be examined, in which the measuring means measures the refraction of the eye to be examined while a subject is visually recognizing the outside through the visible light based on the reflection light of the measurement light beam which is guided to the eye to be examined through the optical system and reflected on the eye to be examined. According to the invention, it is possible to measure the refraction of the eye to be examined while the subject is viewing an object outside the instrument, such as a surrounding ambience of the subject or an image.

In order to achieve the above-mentioned objects, according to the second feature of the invention, there is provided the refraction measuring instrument according to the first feature of the invention in which the optical system includes combining means for combining an optical axis of the measurement light beam with an optical axis of the visible light. According to the invention, the optical axis of the measurement light beam and the optical axis of the visible light from the outside can be combined with each other to perform measurement. Therefore, it is possible to accurately measure the refraction of the eye to be examined, which is visually recognizing the outside.

In order to achieve the above-mentioned objects, according to the third feature of the invention, there is provided the refraction measuring instrument according to the second feature of the invention in which the combining means includes: a free-form-surface prism having a surface for combining the optical axis of the measurement light beam with the optical axis of the visible light by reflection of the measurement light beam and transmission of the visible light; and a deviation angle correcting prism for correcting a deviation angle of the visible light passing through the free-form-surface prism. According to the invention, reductions in size and weight of the instrument can be achieved by using the free-form-surface prism. In addition, a natural image in which deflection or distortion caused when the object located outside the instrument is visually recognized is corrected can be provided by using the deviation angle correcting prism.

In order to achieve the above-mentioned objects, according to the fourth feature of the invention, there is provided the refraction measuring instrument according to the third feature of the invention which further includes a wearing section for enabling the measuring means and the optical system to be worn on a head of the subject. According to the invention, because of reductions in size and weight of the instrument by the use of the free-form-surface prism in the invention described in the third feature of the invention, the instrument can be worn on the head of the subject by the wearing section. The measurement can be performed while the refraction measuring instrument is worn, so that it is possible to perform the measurement in a more natural posture without taking an unnatural posture as in a conventional case where the subject looks through a eyepiece section, thereby reducing a burden on the subject. The measurement can be performed while the subject wearing the instrument is moving.

In order to achieve the above-mentioned objects, according to the fifth feature of the invention, there is provided the refraction measuring instrument according to any one of the first to fourth features of the invention in which the measuring means further includes separating means for separating an optical axis of the measurement light beam from the light source from an optical axis of the reflection light of the measurement light beam which is reflected on the eye to be examined. According to the invention, further reductions in size and weight of the instrument can be achieved. In particular, in the invention described in the third feature of the invention, improved wearing comfort can be provided and physical and mental burdens on the subject can be reduced.

In order to achieve the above-mentioned objects, according to the sixth feature of the invention, there is provided the refraction measuring instrument according to any one of the first to fifth features of the invention in which the measuring means includes: mark projecting means for projecting the measurement light beam from the light source as a mark of a predetermined pattern to the eye to be examined; imaging means for imaging the mark projected as the predetermined pattern by the mark projecting means; and calculating means for calculating the refraction of the eye to be examined based on a shape of the mark imaged by the imaging means. According to the invention, it is possible to provide a specific structure for performing objective refraction measurement on the eye to be examined using the measuring means.

In order to achieve the above-mentioned objects, according to the seventh feature of the invention, there is provided the refraction measuring instrument according to any one of the first to sixth features of the invention which further includes: eye movement measuring the means for measuring eye movement of the eye to be examined; driving means for driving the measuring means; and control means for controlling the driving means to cause the measuring means to follow the eye to be examined based on a result of the eye movement measured by the eye movement measuring means. According to the invention, even when the eye to be examined looks in each direction by the eye movement, accurate measurement can be performed while following the eye to be examined. In particular, in the case of measurement while the subject is moving or measurement while the subject is viewing a moving picture, measurement accuracy can be improved.

In order to achieve the above-mentioned objects, according to the eighth feature of the invention, there is provided the refraction measuring instrument according to the seventh feature of the invention in which the eye movement measuring means includes: an irradiation light source for irradiating the eye to be examined with light; detecting means for detecting an amount of light reflected from a predetermined region close to a limbus of the eye to be examined; and calculating means for calculating a direction and/or a displacement of the eye movement of the eye to be examined based on the amount of light detected by the detecting means, and the control means controls the driving means based on a result calculated by the calculating means. According to the invention, it is possible to provide a specific structure for measuring the eye movement of the eye to be examined.

In order to achieve the above-mentioned objects, according to the ninth feature of the invention, there is provided the refraction measuring instrument according to the eighth feature of the invention in which the calculating means calculates a convergent angle of the eye to be examined based on the amount of light detected by the detecting means. According to the invention, the convergent angle of the eye to be examined, which is one of measurement items important for eye measurement can be obtained, so that an application range of the instrument can be widened.

In order to achieve the above-mentioned objects, according to the tenth feature of the invention, there is provided a refraction measuring instrument which includes a pair of right and left instruments, each of which is the refraction measuring instrument according to any one of the first to ninth features of the invention and measures refraction of each of right and left eyes of the subject. According to the invention, when both the right and left eyes to be examined are measured, there is no burden of replacing the instrument. Both the eyes can be simultaneously measured. Because both the right and left eyes are normally used in actual life, it is possible to perform more reasonable refraction measurement.

BEST MODE FOR CARRYING OUT THE INVENTION

Examples of a refraction measuring instrument according to embodiments of the present invention will be described. The refraction measuring instrument according to the present invention can measure the refraction of the eye to be examined while a subject is moving, unlike a conventional instrument for measuring the refraction of the eye to be examined while the subject is fixedly located in a predetermined position. Therefore, it is possible to measure the refraction in an ambience closer to actual life. In addition, the instrument can be applied to the assessment measurement of various devices based on the structure of a human eye and the action thereof, such as the use of human engineering assessment of a three-dimensional display.

First Embodiment (Structure of Refraction Measuring Instrument)

Figure 1:
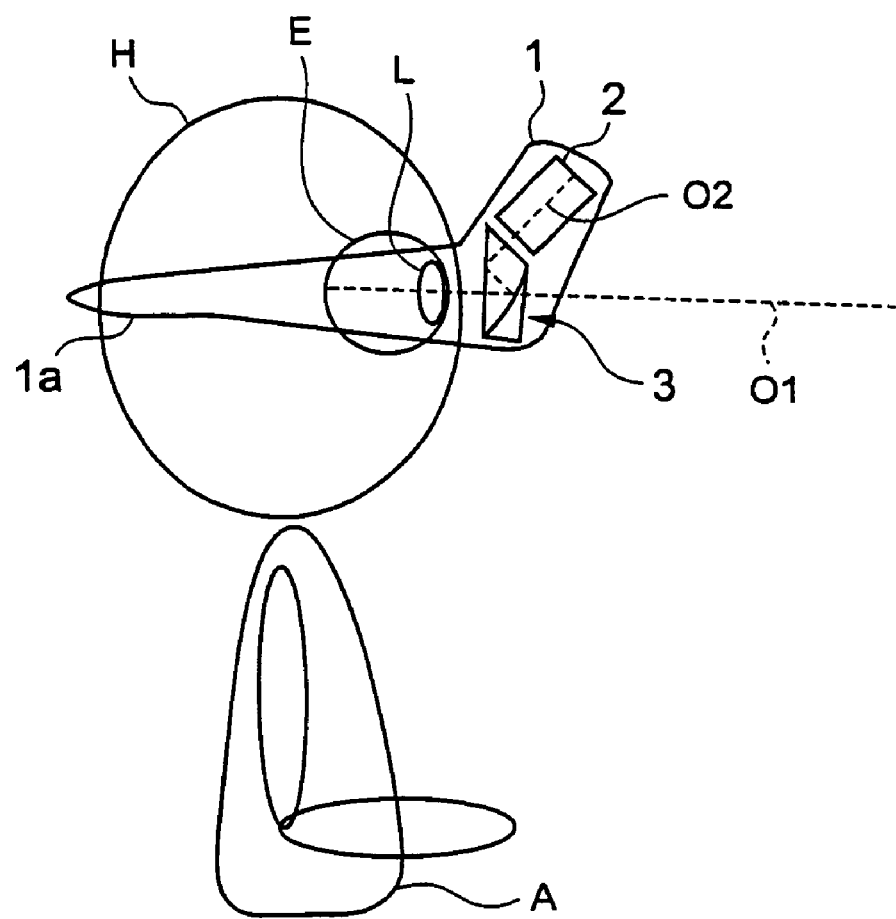
FIG. 1 is a schematic perspective view showing a refraction measuring instrument in use according to a first embodiment of the present invention.
Figure 2:
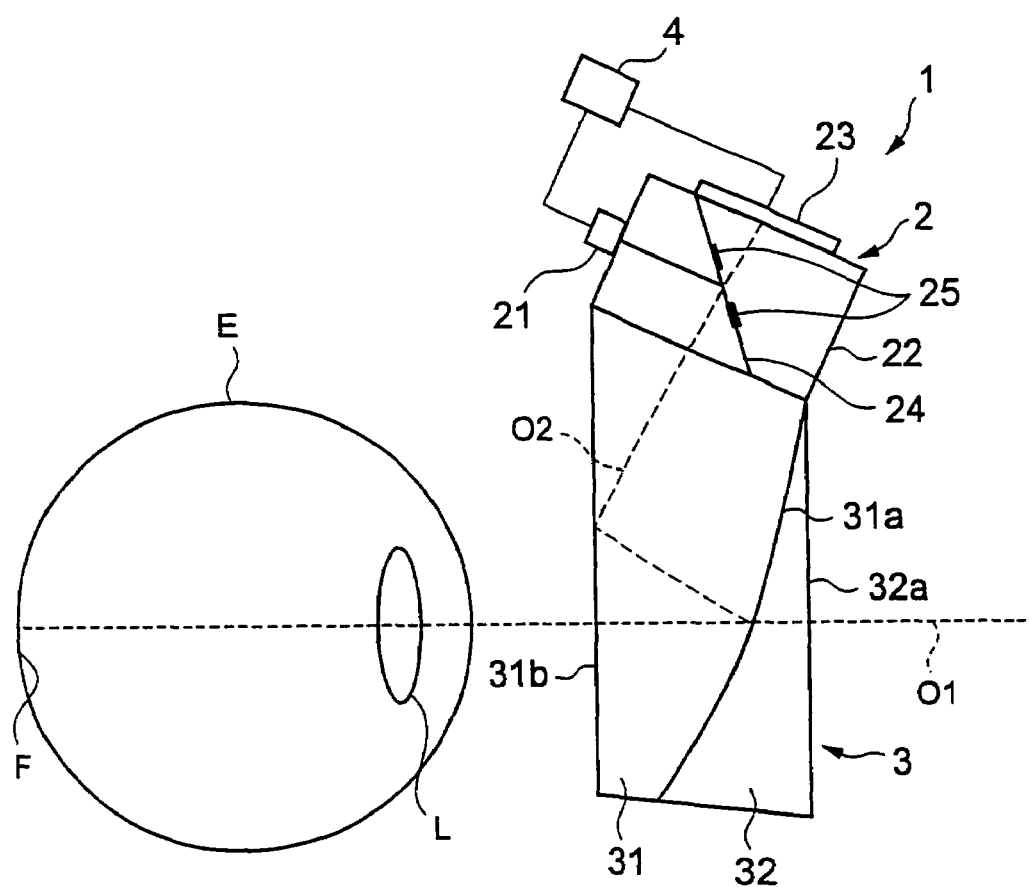
FIG. 2 is a schematic view showing an inner structure of the refraction measuring instrument according to the first embodiment of the present invention.

FIGS. 1 and 2 are structural views showing a refraction measuring instrument 1 according to a first embodiment of the present invention, in which FIG. 1 is a schematic perspective view showing a use state thereof and FIG. 2 is a schematic view showing an inner structure thereof. Each of FIGS. 1 and 2 is a side view, so only the structure of the instrument for the right eye of a subject A is shown therein. However, the same structure is provided for the left eye, so that the refraction of each of the right and left eyes can be measured. Hereinafter, only the structure for the right eye as shown in both the drawings will be described.

As shown in FIG. 1, the refraction measuring instrument 1 performs the measurement while it is worn on a head H of the subject A through a wearing section 1a. The wearing section 1a is composed of a wearing frame similar to a spectacles, a belt whose size can be adjusted according to a size of the head H, and the like. The refraction measuring instrument 1 includes an optical module 2 having an optical system for measuring the refraction of an eye to be examined E and a prism section 3 opposed to (crystalline lens L of) the eye to be examined E. Although will be described in detail later, reference symbol O1 shown in FIG. 1 indicates an optical axis of a light beam passing through the prism section 3 and O2 indicates an optical axis of a light beam reflected on the prism section 3.

Next, the inner section of the refraction measuring instrument 1 will be specifically described with reference to FIG. 2. In FIG. 2, the wearing section 1a is omitted. The refraction measuring instrument 1 includes the optical module 2 and the prism section 3 which are shown in FIG. 1 and a calculation control device 4 for controlling the operation of each section of the instrument and analyzing data imaged by a CCD 23 to be described later to perform the calculation for obtaining the refraction (sphericity, the degree of astigmatism, and astigmatic axis angle) of the eye to be examined E. The calculation control device 4 serves as calculation means and control means in the present invention and includes information processing means such as a CPU and memory means such as a ROM. The calculation control device 4 can be provided outside the refraction measuring instrument 1.

The optical module 2 for performing objective refraction measurement on the eye to be examined E composes measurement means in the present invention and includes a light source 21 for generating a measurement light beam projected to the eye to be examined E for refraction measurement, a prism 22 serving as a beam splitter, and the CCD 23 which has a light receiving surface for receiving reflection light of the measurement light beam on the eye to be examined E and serves as imaging means. The light source 21 is composed of a light emitting diode (LED) for emitting near-infrared light. The prism 22 composing separating means in the present invention is composed of two members which are bonded to each other. An optical axis of the measurement light beam from the light source 21 and the optical axis of the reflection light received by the CCD 23 are separated from each other by a bonding surface 24. A mirror 25 for reflecting the light beam from the light source 21 to project a ring pattern to a fundus F of the eye to be examined E is formed in a ring shape and provided on the bonding surface 24. The mirror 25 composes mark projecting means in the present invention. Note that the mirror 25 is tilted relative to a propagating direction of the measurement light beam and has an ellipsoidal shape (ring shape). A sectional shape of the measurement light beam reflected on the mirror 25 becomes a circular shape (ring shape), thereby forming a circular ring pattern on the fundus F. In the present invention, the word "a ring shape" is used in referring to such a meaning (same as above).

The prism section 3 of the refraction measuring instrument 1 composes an optical system and combining means in the present invention and includes a free-form-surface prism 31 which is opposed to the eye to be examined E and has a rotational asymmetric shape, and a deviation angle correcting prism 32 bonded to the surface of the free-form-surface prism 31 which is located on an opposite side of the eye to be examined E. For example, when a dielectric evaporation film is formed on a surface (beam splitting surface) 31a of the free-form-surface prism 31 which is located on the opposite side of the eye to be examined E, the prism 31 acts as a dichroic prism for transmitting (main part of) visible light and reflecting infrared light. The deviation angle correcting prism 32 is made of a material having the same transmittance as that of the free-form-surface prism 31 (the same material is enough), formed such that a surface 32a located farthest from the eye to be examined E becomes parallel to a surface 31b of the free-form-surface prism 31 which is opposed to the eye to be examined E, and corrects a deviation angle of visible light passing through the free-form-surface prism 31. The measurement light beam from the light source 21 and visible light incident on the instrument from an outside are simultaneously guided to the eye to be examined E by the prism section 3.

Note that the light source 21 and the fundus F are located based on an optically conjugate relationship and the CCD 23 and the fundus F are located based on an optically conjugate relationship.

(Action and Operation of Refraction Measuring Instrument)

The action and the operation of the refraction measuring instrument 1 having the above-mentioned structure will be described. First, the wearing section 1a is adjusted according to the size of the head H of the subject A and the refraction measuring instrument 1 is worn on the head H such that the surface 31b of the free-form-surface prism 31 of the prism section 3 is opposed to the eye to be examined E. At this time, the subject A can visually recognize the surrounding ambience, the (three-dimensional) display, or the like through the prism section 3 transmitting the visible light. A visual image is recognized as an image without deflection or distortion by the deviation angle correcting prism 32.

When a switch which is not shown is pressed down, the light source is turned on by the control of the calculation control device 4. The measurement light beam emitted from the light source 21 is reflected on the mirror 25 formed in the ring shape to become a ring (in section) light beam. The ring light beam propagates along the optical axis O2 and is incident on the free-form-surface prism 31 of the prism section 3. The ring measurement light beam is reflected on the surface 31b of the free-form-surface prism 31 and the beam splitting surface 31a thereof and propagates on the optical axis O1. Then, the light beam is incident on the eye to be examined E, thereby forming the ring pattern on the fundus F.

The measurement light beam reflected on the fundus F exits from the eye to be examined E and propagates along the optical axis O1. The light beam is reflected on the beam splitting surface 31a of the free-form-surface prism 31 and the surface 31*b* thereof and received by the CCD 23 through the bonding surface 24 of the prism 22 of the optical module 2. Therefore, the ring pattern formed on the fundus F is imaged. Data obtained by the CCD 23 is sent to the calculation control device 4. A size of the ring pattern is analyzed to calculate the sphericity. When the ring pattern is distorted to an ellipsoidal shape, the degree of astigmatism is calculated based on the degree of distortion. The astigmatic axis angle is calculated based on the orientation of the ellipsoidal shape.

According to the above-mentioned refraction measuring instrument 1, reductions in size and weight of the instrument are achieved because the free-form-surface prism 31 is used. Therefore, it is possible to perform the refraction measurement in a natural posture in which the instrument is worn on the subject A. The refraction can be measured while the surrounding ambience, the three-dimensional display, or the like is clearly and visually recognizable. It is also possible to measure the refraction while the subject wearing the instrument is moving.

When the surrounding ambience or a stereoscopic image on the three-dimensional display is being viewed, a point which the subject A is visually recognizing can be determined based on the degree of accommodation of the eye to be examined E. In other words, the degree of accommodation of the eye to be examined E can be determined from a result obtained by measurement of the refraction. Therefore, it is possible to determine the degree of depth of an object which the subject A is visually recognizing. When an eye movement measuring apparatus to be described later (see a third embodiment) is used, the direction in which the eye to be examined E gazes can be measured and a three-dimensional position of the object which the subject A is visually recognizing can be determined. Eye fatigue caused while the three-dimensional display is observed may result from the conflict between convergence and accommodation. Whether or not the conflict is caused can be examined.

Unlike a conventional structure in which a position of an object which the subject is visually recognizing is determined based on a convergent angle of both the right and left eyes, a position of the object which is being visually recognized by each of the right and left eyes of the subject can be determined to measure the accommodation capability of each of the eyes. Therefore, it is possible to obtain more detailed information related to the eye to be examined.

Second Embodiment

Figure 3:
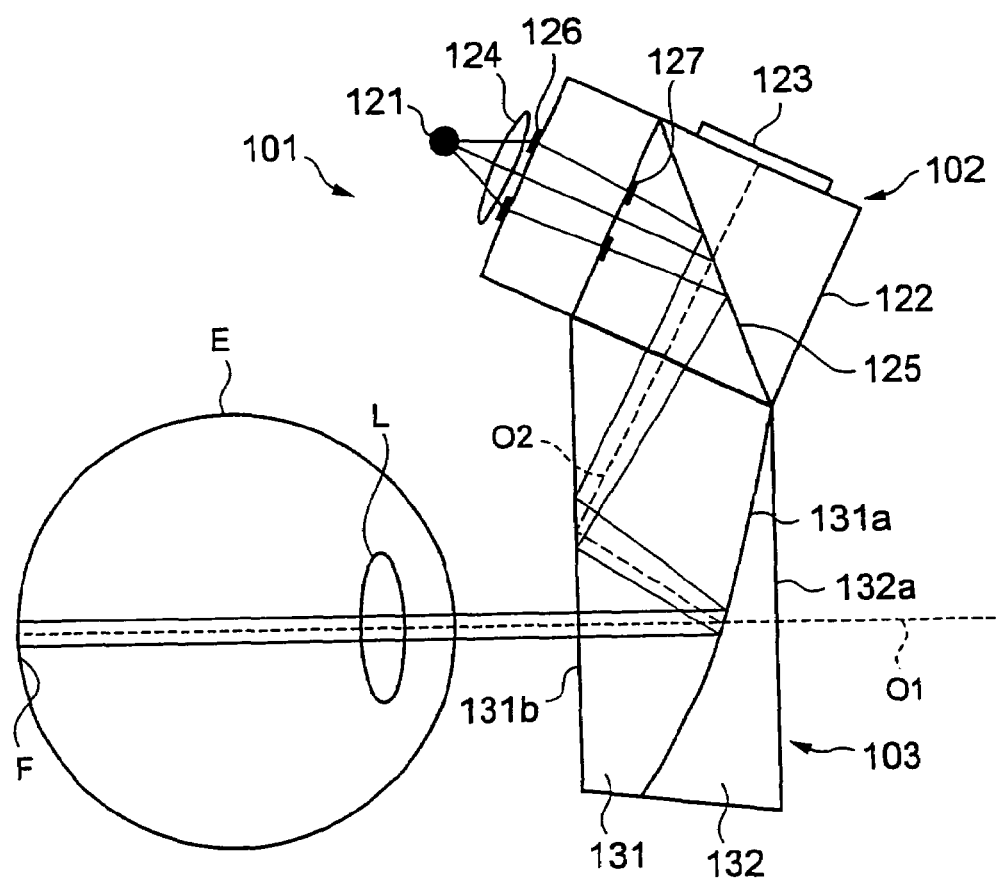
FIG. 3 is a schematic view showing an inner structure of a refraction measuring instrument according to a second embodiment of the present invention.

Next, a refraction measuring instrument according to a second embodiment of the present invention will be described. FIG. 3 is a schematic view showing an inner structure of a refraction measuring instrument 101 according to this embodiment. Although not shown, the refraction measuring instrument 101 is provided with a wearing section for enabling the instrument to be worn on the head of the subject and used in the same state as that of the refraction measuring instrument 1 according to the first embodiment.

(Structure of Refraction Measuring Instrument)

As shown in FIG. 3, the refraction measuring instrument 101 according to this embodiment includes an optical module 102 and a prism section 103. Although not shown, the instrument includes the same calculation control device (calculation means and control means) as that of the refraction measuring instrument 1 according to the first embodiment.

The optical module 102 (measurement means) for performing refraction measurement on the eye to be examined E includes a light source 121 for generating a measurement light beam projected to the eye to be examined E to measure the refraction, a prism 122 serving as a beam splitter, a CCD 123 which has a light receiving surface and serves as imaging means, and a lens 124 for refracting the measurement light beam from the light source 121. The light source 121 and the CCD 123 have the same structures as those of the refraction measuring instrument 1 according to the first embodiment. Reference numeral 125 denotes a bonding surface between two members composing the prism 122. The prism 122 acts as a beam splitter (separating means) because of the bonding surface 125.

The optical module 102 includes a ring-shaped diaphragm 126 located in an optically conjugate position with the pupil of the eye to be examined E and a ring-shaped diaphragm 127 located in an optically conjugate position with the fundus F. The measurement light beam from the light source 121 is projected as a light beam having a ring section to the eye to be examined E by the diaphragms 126 and 127 composing mark projecting means in the present invention.

The prism section 103 (optical system and combining means) of the refraction measuring instrument 101 includes a free-form-surface prism 131 and a deviation angle correcting prism 132 as in the refraction measuring instrument 1 according to the first embodiment. A bonding surface between the free-form-surface prism 131 and the deviation angle correcting prism 132 composes a beam splitting surface 131*a* for transmitting visible light and reflecting infrared light. A surface 131*b* of the free-form-surface prism 131 which is opposed to the eye to be examined E is made parallel to a surface 132*a* of the deviation angle correcting prism 132.

Reference symbol O1 indicates the optical axis of a light beam passing through the prism section 103 and O2 indicates the optical axis of a light beam reflected on the prism section 103. The measurement light beam from the light source 121 and visible light incident on the instrument from an outside are simultaneously guided to the eye to be examined E by the prism section 103.

(Action and Operation of Refraction Measuring Instrument)

Subsequently, the action and the operation of the refraction measuring instrument 101 having the above-mentioned structure according to this embodiment will be described. The measurement light beam of near-infrared light which is emitted from the light source 121 is guided to the lens 124 and passes through the diaphragm 126 located in the conjugate position with the pupil of the eye to be examined E and the diaphragm 127 located in the conjugate position with the fundus F to become a ring (in section) light beam. The light beam is reflected on the bonding surface 125 of the prism 122, deflected in an optical axis O2 direction, and propagates to the prism section 103 side.

The ring measurement light beam incident on the prism section 103 is reflected on the surface 131*b* of the free-form-surface prism 131 and the beam splitting surface 131*a* thereof and propagates on the optical axis O1. Then, the light beam is incident on the eye to be examined E. The ring measurement light beam guided to the eye to be examined E forms a ring pattern on the fundus F located in the conjugate position with the diaphragm 127.

At this time, the surrounding ambience of the subject or a displayed image is visually recognized by the subject through the visible light which passes through the prism section 103 and propagates on the optical axis O1.

The measurement light beam reflected on the fundus F of the eye to be examined E exits from the eye to be examined E and propagates along the optical axis O1. The light beam is reflected on the beam splitting surface 131*a* of the free-formsurface prism 131 and the surface 131b thereof and received by the CCD 123 through the bonding surface 125 of the prism 122 of the optical module 102. Therefore, the ring pattern formed on the fundus F is imaged. The calculation control device which is not shown analyzes a shape of the ring pattern on the fundus F which is imaged by the CCD 123 and calculates the sphericity, the degree of astigmatism, and the astigmatic axis angle.

According to the above-mentioned refraction measuring instrument 101, as in the refraction measuring instrument 1 described in the first embodiment, it is possible to perform the refraction measurement in a natural posture in which the instrument is worn on the subject. The refraction of an eye to be examined can be measured while a subject is viewing an object outside the instrument. It is also possible to measure the refraction while the subject wearing the instrument is moving. A position of an object which is being visually recognized can be also determined for each eye.

The refraction measuring instrument 1 according to the first embodiment of the present invention and the refraction measuring instrument 101 according to the second embodiment of the present invention can be modified as follows.

First, a pattern projected to the fundus is not limited to the above-mentioned ring pattern and thus various patterns which are usable for objective measurement can be employed.

Suitable selection of measurement items can be made according to purposes and applications. For example, in addition to measurement on the sphericity, the degree of astigmatism, and the astigmatic axis angle, high-order wavefront aberration is measured using a Hartmann-Shack wavefront sensor.

The subject does not visually recognize a predetermined object at all times. For example, when the measurement is to be performed while the subject is moving, the degree of accommodation (refraction) of the eye to be examined E is changed with a change in relative position between the object and the eye to be examined E. Therefore, a shape of the ring pattern on the fundus F momentarily changes. When a moving object in a stereoscopic image displayed on the three-dimensional display is traced by the eyes, the shape of the ring pattern changes as in the above-mentioned case.

If the refraction of the eye to be examined E, which changes with time can be measured in real time, it is very effective in not only the case of purposing the prescribing of spectacles or the like but also the case where the human engineering assessment measurement of a display is performed. Therefore, the instrument can be constructed such that the optical module is controlled by the calculation control device to repeatedly measure the refraction a predetermined number of times per second (which can be determined according to the calculation speed of the calculation control device) and the calculation is performed.

Third Embodiment

When the refraction of the eye to be examined E is measured in real time as described above, the eye movement of the eye to be examined E particularly becomes a problem with respect to measurement accuracy in many cases. For example, when the measurement using retinoscopy is performed by the refraction measuring instrument 1 according to the first embodiment, the measurement accuracy is less affected by small eye movement. However, when the eye movement is large or when an eye position is to be detected with high accuracy using a Hartmann-Shack wavefront sensor, it is necessary to provide any structure for moving the instrument based on the eye movement to ensure the measurement accuracy. With respect to an eye movement measuring method enabling this, there are a method using reflection light on the anterior surface of a cornea, a method using reflection light on the posterior surface of the cornea or the anterior or posterior surface of a crystalline lens, a method of detecting the outside edge of a pupil, a method of tracking a limbus (boundary between a white sclera and a dark iris), or the like. A gaze direction of the eye to be examined E can be also measured using a combination of those methods. Hereinafter, the refraction measuring instrument 1 according to the first embodiment to which a structure for tracking the limbus to measure the eye movement is added will be described with reference to FIGS. 4 and 5. The same names and reference symbols are used for the portions described in the first embodiment without any changing.

(Structure of Eye Movement Measuring Apparatus)

Figure 4:
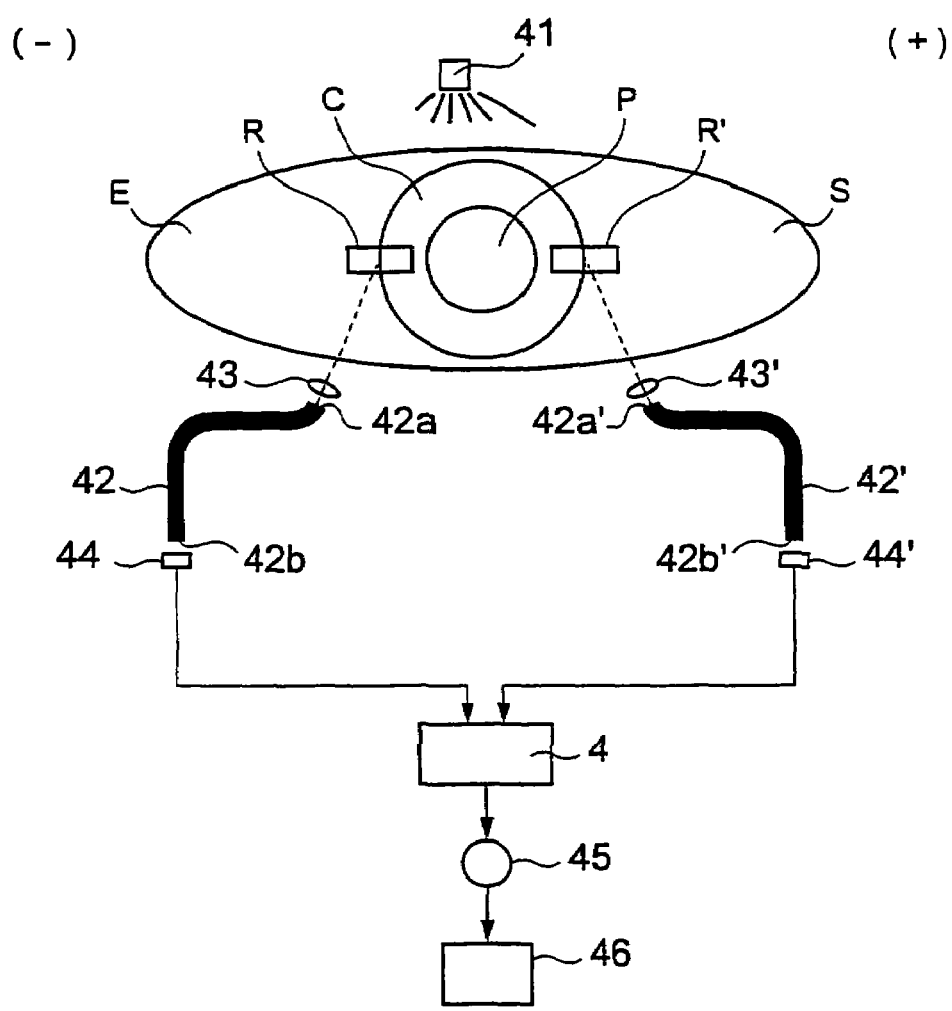
FIG. 4 is a schematic diagram showing a structure of an eye movement measuring apparatus provided for a refraction measuring instrument according to a third embodiment of the present invention.

FIG. 4 illustrates a schematic structure of an eye movement measuring apparatus for measuring the eye movement of the eye to be examined E. The eye movement measuring apparatus composes eye movement measuring means in the present invention and includes a light source 41 (irradiation light source) for irradiating the eye to be examined E with (for example) near-infrared light, an optical fiber 42 for guiding reflection light of the near-infrared light from the light source 41 which is reflected on a rectangular region R of the eye to be examined E, a lens 43 for converging the reflection light to an end surface 42a of the optical fiber 42 which is located on the side of the eye to be examined E, and a photo detector 44 (detecting means) for detecting the amount of reflection light which is guided by the optical fiber 42 and exits from an end surface 42b. Similarly, an optical fiber 42', a lens 43', and a photo detector 44' are provided to detect reflection light of the near-infrared light from the light source 41 which is reflected on a rectangular region R'. The optical fibers 42 and 42' are tilted relative to the rectangular regions R and R' because the view field of the subject A which is visually viewing the surrounding ambience or the display through the prism section 3 of the refraction measuring instrument 1 is prevented from being obstructed.

The rectangular region R and the end surface 42a of the optical fiber 42 are located in optically conjugate positions with respect to the lens 43. The rectangular region R' and the end surface 42a' of the optical fiber 42 are located in optically conjugate positions with respect to the lens 43'. Each of the end surfaces 42a, 42b, 42a', and 42b' of the optical fibers 42 and 42' becomes a rectangular shape as in the rectangular regions R and R'. A shape of the region on the eye to be examined E, which is employed for detecting the reflection light of the near-infrared light from the light source 41 is not limited to a rectangle and thus, for example, a circle or an ellipse may be used. In this time, the optical fibers 42 and 42' provided with end surfaces each having the same shape as that of the employed region are used.

The calculation control device 4, which corresponds to the calculation means and the control means in the present invention, calculates a difference between the amounts of reflection light detected by the photo detectors 44 and 44' to determine the gaze direction, that is, a right direction or a left direction, of the eye to be examined E and transmits a signal corresponding to a result obtained by the determination to an output terminal 45. An ultrasonic motor 46 which acts as driving means in the present invention is provided to drive the optical module 2 in the right-and-left directions relative to the prism section 3 and operated based on the signal transmitted to the output terminal 45. A separate calculation circuit for performing the calculation may be provided.

For example, the calculation control device 4 subtracts the amount of light detected by the photo detector 44' from the amount of light detected by the photo detector 44, determines a driving direction of the optical module 2 and a displacement thereof which correspond to a sign (+/−) of a subtraction value and an absolute value thereof, respectively, and transmits a signal indicating the driving direction and the displacement to the output terminal 45. The ultrasonic motor 46 is operated based on the signal transmitted to the output terminal 45 to drive the optical module 2 in the driving direction by the displacement.

In FIG. 4, reference symbol P indicates a pupil of the eye to be examined E, C indicates a cornea (iris), and S indicates a sclera. When the eye to be examined E faces the front, the rectangular regions R and R' on the eye to be examined E are initially set such that the boundary between the cornea C and the sclera S is located at the center of each of the regions, that is, such that a half of each of the rectangular regions R and R' is included in the cornea C side and the remaining half is included in the sclera S side. Therefore, each of the rectangular regions R and R' is located across the dark iris (cornea C) and the white sclera (sclera S).

(Action and Operation of Eye Movement Measuring Apparatus)

Subsequently, the action of the eye movement measuring apparatus having the above-mentioned structure will be described. When the light source 41 is turned on to irradiate the eye to be examined E with the near-infrared light, reflection light on the rectangular regions R and R' are condensed to the end surfaces 42a and 42a' of the optical fibers 42 and 42' through the lenses 43 and 43'. The condensed light are guided through the optical fibers 42 and 42', exit from the end surfaces 42b and 42b', and are detected by the photo detectors 44 and 44'.

At this time, when the eye to be examined E faces the front, a half of each of the rectangular regions R and R' is included in the cornea C side and the remaining half is included in the sclera S side. Therefore, the amounts of reflection light detected by the photo detectors 44 and 44' become equal to each other, so the difference between the amounts of light which is calculated by the calculation control device 4 becomes (substantially) zero. Thus, a displacement for driving the optical module 2 is determined to be zero and this result is transmitted as a signal to the output terminal 45. The ultrasonic motor 46 acts so as not to drive the optical module 2 based on the signal (difference is zero) transmitted to the output terminal 45.

When the eye to be examined E views the left in FIG. 4, an area of the dark iris portion within the rectangular region R increases and an area of the white sclera portion reduces. In contrast to this, an area of the dark iris portion within the rectangular region R' reduces and an area of the white sclera portion increases. In view of reflectance of the near-infrared light on the dark iris portion and the white sclera portion, the white sclera portion has larger reflectance. Therefore, the amount of light reflected from the rectangular region R and detected by the photo detector 44 reduces. In contrast to this, the amount of light reflected from the rectangular region R' and detected by the photo detector 44' increases. As a result, a sign of the difference value calculated by the calculation control device 4 becomes minus (−). Thus, the driving direction of the optical module 2 is determined to be a minus side (left side in FIG. 4), the displacement for driving is determined based on an absolute value of the difference value, and this result is transmitted as a signal to the output terminal 45. The ultrasonic motor 46 acts to drive the optical module 2 in the minus direction by the displacement based on the signal transmitted to the output terminal 45.

When the eye to be examined E views the right in FIG. 4, an area of the white sclera portion within the rectangular region R increases and an area of the dark iris portion reduces. In contrast to this, an area of the white sclera portion within the rectangular region R' reduces and an area of the dark iris portion increases. Therefore, the amount of light reflected from the rectangular region R and detected by the photo detector 44 increases. In contrast to this, the amount of light reflected from the rectangular region R' and detected by the photo detector 44' reduces. As a result, a sign of the difference value calculated by the calculation control device 4 becomes plus (+). Thus, the driving direction of the optical module 2 is determined to be a plus side (right side in FIG. 4), the displacement for driving is determined based on an absolute value of the difference value, and this result is transmitted as a signal to the output terminal 45. The ultrasonic motor 46 acts to drive the optical module 2 in the plus direction by the displacement based on the signal transmitted to the output terminal 45.

According to the eye movement measuring apparatus of the limbus tracking type, the outputs of the photo detectors are subjected to only analog processing without relatively complex processing such as image analysis, so that high-speed processing can be performed. In practice, limbus tracking of 1000 times (1 kHz) or more per second is possible. Therefore, even when high-speed eye movement is caused, the measurement light beam from the light source 21 can be located in the fovea of a retina, so that it is possible to perform accurate refraction measurement in real time.

It is unnecessary to perform alignment with the eye to be examined E by driving the optical module 2 for each calculation processing repeated at high speed. An operating timing may be controlled so as to drive the optical module 2, for example, one time or several times per second. According to the control, it is unnecessary to perform waste alignment operation corresponding to the instantaneous movement of a sight line of the subject A and the failure of the apparatus or the wastage thereof can be reduced.

The following structure may be used. Thresholds are provided stepwise for the calculated difference value. When the absolute value of the difference value is within a minimal threshold range, the optical module 2 is not driven. Respective displacements for driving are set corresponding to the other threshold ranges. When the absolute value of the difference value is within a measurable range, misalignment is allowed. A range of each of the thresholds can be set to the difference value corresponding to a displacement of the eye to be examined, which is equal to a width of the light receiving surface of the CCD 23, for example. According to such a structure, the ring pattern on the fundus F can be constantly imaged by the CCD 23.

The eye movement measuring apparatus in this embodiment does not require a large-size member. Therefore, even when this apparatus is provided for the refraction measuring instrument 1, a burden is not applied to the subject A during measurement.

A convergent angle of both the right and left eyes to be examined or convergent angles of the respective right and left eyes to be examined may be calculated based on the respective gaze directions of the right and left eyes to be examined, which are obtained by the eye movement measuring apparatus in this embodiment. The eye to be examined E, which is irradiated by the light source 41 can be also imaged by the CCD 23 to measure a size of the pupil from the anterior segment image.

In this embodiment, a structure is employed in which the reflection light on the two regions of the eye to be examined E are detected to measure the eye movement in the right-and-left directions and the optical module 2 is driven according to right and left movements of the eye based on a result obtained by the measurement. In order to deal with the eye movement in up-and-down directions, the positions of the regions or the number of regions may be changed. A structure can be also used in which the prism section 3 is integrally driven with the optical module 2.

Figure 5:
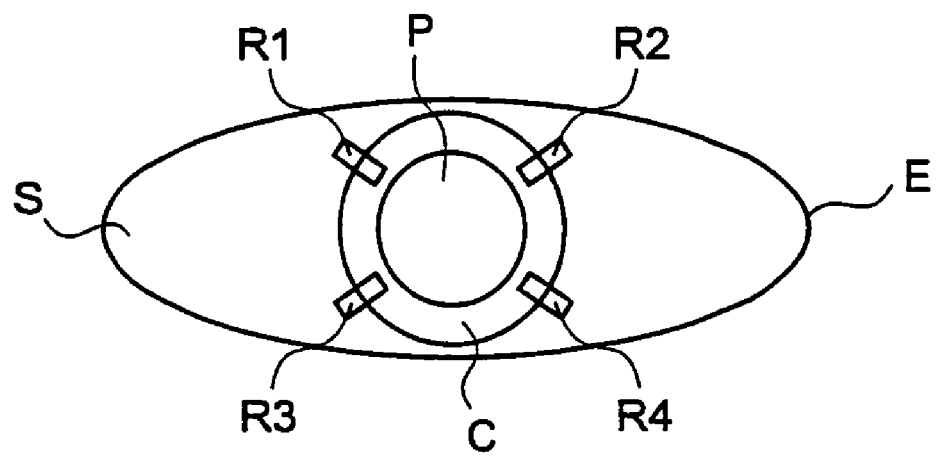
FIG. 5 is a schematic view showing a partial structure of a modified example of the eye movement measuring apparatus provided for the refraction measuring instrument according to the third embodiment of the present invention.

As shown in FIG. 5, for example, reflection light of the near-infrared light from the light source 41 (not shown) which are reflected on four rectangular regions R1, R2, R3, and R4 of the eye to be examined E can be detected to perform the alignment of the optical module 2 in the up-and-down and right-and-left directions. In this case, assume that the rectangular regions R1 and R4 located in diagonal positions are set as a pair and the rectangular regions R2 and R3 are set as a pair. The calculation control device 4 calculates $\Delta 1$ (=(amount of light reflected from the rectangular region R1)– (amount of light reflected from the rectangular region R4)) and $\Delta 2$ (=(amount of light reflected from the rectangular region R2)–(amount of light reflected from the rectangular region R3)). When $\Delta 1 = \Delta 2 = 0$, it is determined that the eye to be examined E faces the front. When $\Delta 1 > 0$ and $\Delta 2 > 0$, it is determined that the eye to be examined E faces downward. When $\Delta 1 < 0$ and $\Delta 2 < 0$, it is determined that the eye to be examined E faces upward. When $\Delta 1 > 0$ and $\Delta 2 < 0$, it is determined that the eye to be examined E faces the right in FIG. 5. When $\Delta 1 < 0$ and $\Delta 2 > 0$, it is determined that the eye to be examined E faces the left. A signal corresponding to each of results obtained by the determination is transmitted to the output terminal 45. The ultrasonic motor may be operated to drive the optical module 2 based on the signal transmitted to the output terminal 45. It may be determined that the eye to be examined E faces the upper right, the upper left, the lower right, or the lower left based on absolute values of $\Delta 1$ and $\Delta 2$. The displacement for driving is calculated from the absolute values of $\Delta 1$ and $\Delta 2$ as in the case of the second embodiment.

When the four regions are set as described above, it is necessary to provide four optical fibers and four lenses corresponding to the regions. In addition, an ultrasonic motor for driving the optical module 2 in the up-and-down directions and an ultrasonic motor for driving the optical module 2 in the right-and-left directions are provided and separately driven.

Each of the refraction measuring instruments described above has the structure for performing the refraction measurement on both the right and left eyes to be examined. A structure for performing the measurement on only one of the eyes may be used.

The driving means for driving the optical module is not limited to the above-mentioned ultrasonic motor and thus can be freely selected according to purposes.

A size of the instrument can be reduced by using the free-form-surface prism, so the structure in the present invention can be applied to a stationary refraction measuring instrument to achieve space saving. The refraction measuring instrument in the present invention can be also constructed as a portable refraction measuring instrument.

A structure for measuring a pupillary distance (PD value) between the right and left eyes and moving an optical system including the free-form-surface prism based on the measured PD value may be provided for the refraction measuring instrument capable of measuring both the right and left eyes to be examined as described in each of the above-mentioned embodiments. For example, it is possible to use a structure in which a scale for PD value measurement is provided outside the instrument to measure a PD value by the subject or the like and respective optical systems are moved in the right-and-left directions based on the PD value. In addition, it is possible to use not such a structure based on manual operation but a structure for detecting the pupils of both the right and left eyes to be examined from images of the eyes to be examined, each of which is obtained by the CCD and calculating a distance between the centers of the pupils to obtain a PD value and a structure in which means (including ultrasonic motors) for separately driving right and left optical systems in the right-and-left directions are provided to move the optical systems based on the obtained PD value.

The refraction measuring instruments described in the embodiments of the present invention are examples of specific structures for describing the spirit of the present invention in detail. Therefore, any modifications and additions can be made without departing from the spirit of the present invention.

INDUSTRIAL APPLICABILITY

According to the present invention with respect to the above-mentioned structures, it is possible to provide a refraction measuring instrument capable of measuring the refraction of an eye to be examined while a subject is viewing an object outside the instrument, such as the surrounding ambience of the subject or an image.

According to the present invention, it is possible to provide a refraction measuring instrument capable of measuring the refraction of the eye to be examined in a more natural posture.

According to the present invention, it is possible to provide a refraction measuring instrument capable of measuring the refraction even when a subject is moving.

According to the refraction measuring instrument, it is possible to perform real time measurement on the refraction of the eye to be examined, which changes with time.

The invention claimed is:

1. A refraction measuring instrument comprising:
   measuring means that has a light source for emitting a measurement light beam to an eye to be examined and performs objective measurement on refraction of the eye to be examined based on reflection light of the measurement light beam emitted from the light source, which is reflected on the eye to be examined; and
   an optical system, to which the light source and the measuring means are added, for simultaneously guiding the measurement light beam emitted from the light source and visible light incident thereon from an outside to the eye to be examined,
   wherein the optical system comprises a free-form-surface prism having a surface for combining the optical axis of the measurement light beam with the optical axis of the visible light by reflection of the measurement light beam and transmission of the visible light, and a deviation angle correcting prism for correcting a deviation angle of the visible light passing through the free-form-surface prism,
   wherein the light source emits the measurement light beam to be incident on the optical system from the direction different from that of the visible light,
   wherein the free-form-surface prism reflects the incident measurement light beam inside itself, so that the measurement light beam is incident on the eye to be examined, and reflects the reflection light from the eye to be examined inside itself to the direction different from that of the visible light, in order to output the reflection light to the measurement means, and wherein the measuring means measures the refraction of the eye to be examined while a subject is visually recognizing the outside through the visible light based on the reflection light of the measurement light beam which is guided to the eye to be examined through the optical system and reflected on the eye to be examined.

2. The refraction measuring instrument according to claim 1 wherein the measuring means comprises:

mark projecting means for projecting the measurement light beam from the light source as a mark of a predetermined pattern to the eye to be examined;

imaging means for imaging the mark projected as the predetermined pattern by the mark projecting means; and calculating means for calculating the refraction of the eye to be examined based on a shape of the mark imaged by the imaging means.

3. The refraction measuring instrument according to claim 1 further comprising a wearing section for enabling the measuring means and the optical system to be worn on a head of the subject.

* * * * *